United States Patent [19]

Ware

[11] 4,142,532

[45] Mar. 6, 1979

[54] BODY IMPLANTABLE STIMULATOR WITH NOVEL CONNECTOR AND METHOD

[75] Inventor: Lyle A. Ware, Bloomington, Minn.

[73] Assignee: Medtronic, Inc., Minneapolis, Minn.

[21] Appl. No.: 894,358

[22] Filed: Apr. 7, 1978

[51] Int. Cl.² ............................................... A61N 1/00
[52] U.S. Cl. .................................................. 128/419 P
[58] Field of Search ........ 128/419 P, 419 PG, 419 PS

[56] References Cited

U.S. PATENT DOCUMENTS

| | | | |
|---|---|---|---|
| 3,683,932 | 8/1972 | Cole .................................. | 128/419 P |
| 3,822,707 | 7/1974 | Adducci et al. .................. | 128/419 P |

*Primary Examiner*—William E. Kamm

*Attorney, Agent, or Firm*—Wayne A. Sivertson

[57] ABSTRACT

A body implantable stimulator having a signal generator and lead electrically and mechanically interconnected by a preformed connector. The connector carries terminals to establish electrical communication between the signal generator and the lead, passageways being provided in the connector body to accept and guide the signal generator output connections and lead into contact with the terminals. In a preferred embodiment, the terminals are provided with intersecting bores such that an output connection and lead contact each other within a terminal. The preformed connector may be mechanically fastened to the signal generator.

24 Claims, 4 Drawing Figures

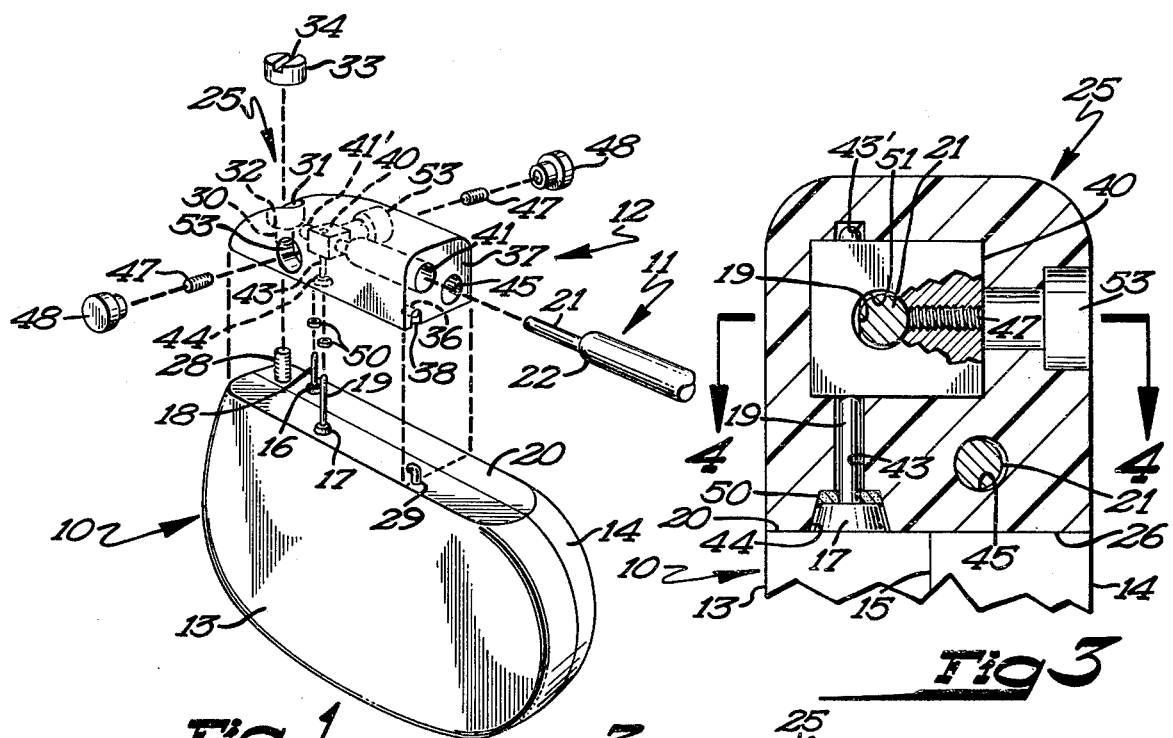
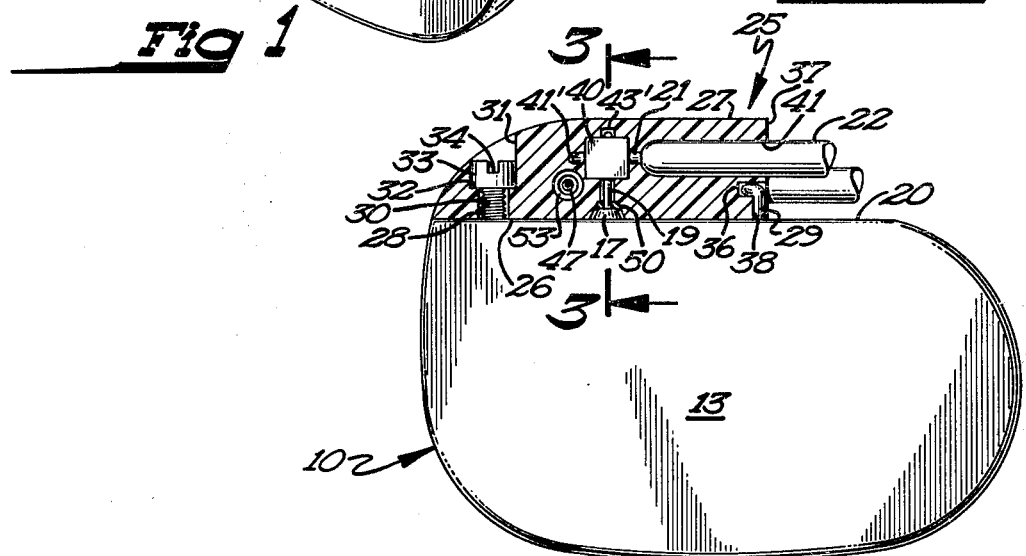
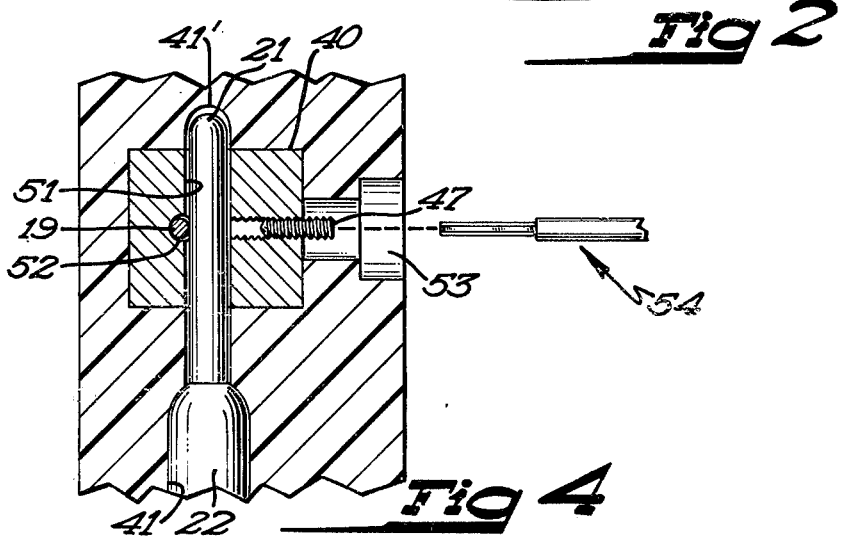

BODY IMPLANTABLE STIMULATOR WITH NOVEL CONNECTOR AND METHOD

BACKGROUND OF THE INVENTION

Body implantable stimulators are known to the prior art, the most common being the cardiac pacemaker. Typically, such stimulators are formed of a separable lead and signal generator with provision being made to electrically and mechanically interconnect the lead and generator to complete the stimulator unit.

Many prior art signal generators have been formed by molding the components, including mechanical and electrical connections for the lead, in a matrix of encapsulating material which supports the components and shields them from the body environment. Typically, the encapsulating material is an epoxy.

In the body environment, it is generally recognized that an enclosed and hermetically sealed signal generator is more reliable as a result of the known and controlled environment provided by the hermetic seal. For this reason, many recent signal generator designs include a rigid enclosure formed of a plurality of preformed members which are typically welded together to complete the enclosure. The interconnection between the generator and the lead, when it is desired that these members be separable, occurs outside of such an enclosure. While it is common to mold an interconnect assembly from epoxy, such a process diminishes another benefit of a preformed enclosure — elimination of the epoxy encapsulation process. Thus a preformed interconnect assembly, which may be reliably secured to a preformed enclosure housing the generator components, would greatly facilitate assembly of the stimulator. The amount of handling would be reduced with the remaining handling being easier to perform than an epoxy molding process. A preformed interconnect assembly is disclosed in application Ser. No. 793,642, filed May 4, 1977 in the name of Richard A. Jones, which application is commonly owned with the present application.

The above referenced application provides a preformed interconnect assembly thereby eliminating the necessity of forming that assembly in place, as by an epoxy molding process, for example. However, that assembly still requires the use of epoxy, or some similar substance, to adhere it to the signal generator enclosure. Additionally, the electrical connection between the interconnect assembly terminal and the signal generator requires manipulation of a wire to position it and a weld, or other similar process, to secure it in position. Thus, while the interconnect assembly of the above referenced application greatly reduces the handling necessary to form and position an interconnect assembly on a signal generator unit, considerable handling remains necessary.

SUMMARY OF THE INVENTION

The present invention provides a preformed interconnect assembly which may be mechanically secured to a signal generator thereby eliminating the necessity of epoxy or other similar substances to adhere the assembly to the generator. Additionally, the electrical interconnection to the signal generator is greatly facilitated. Accordingly, the amount of handling necessary to assemble the stimulator and establish the proper electrical connections is greatly reduced. In a preferred embodiment, a preformed interconnect assembly or connector is provided with passageways which accept and guide the signal generator output connections and the lead into electrical communication with a terminal. The terminals are provided with intersecting bores such that an output connection and lead contact each other within a terminal. Means are provided for securing the signal generator output connections and the lead within the terminal. In a preferred embodiment, this securement is accomplished via a set screw which engages the lead contact to urge it against the signal generator output connection.

BRIEF DESCRIPTION OF THE DRAWINGS

FIG. 1 is an exploded view of a preferred embodiment of the present invention.

FIG. 2 is a partial cutaway of the embodiment of FIG. 1, as assembled.

FIG. 3 is a cross section taken along the line 3—3 in FIG. 2.

FIG. 4 is a cross section taken along the line 4—4 in FIG. 3.

DETAILED DESCRIPTION OF THE DRAWINGS

Referring now to FIG. 1, there is illustrated an exploded view of a preferred embodiment of the present invention including generally an implantable signal generator 10, lead 11, an interconnect assembly or connector 12. Signal generator 10 includes all the necessary signal generating components and power sources within an enclosure formed of two body members 13 and 14 jointed together at a seam 15 in known manner, as by welding, for example. Electrical feed throughs 16 and 17 provide electrical communication with the enclosed signal generating components, in known manner, the feed throughs having electrical connections 18 and 19. The feed throughs 16 and 17 extend from a platform 20 which is adapted to receive the interconnect assembly 12 in a manner to be described more fully below. Lead 11 is of the type having a pin connection 21 and insulating body 22 which surrounds and protects an electrical conductor (not shown).

The interconnect assembly or connector 12 includes a body portion 25 which may be formed in any known manner, as by molding, for example. Preferably, the body 25 is of a clear material so as to allow visual verification of the electrical connections. The body 25 may be formed of many known materials including, polysolfone as sold under the trademark UDEL by Union Carbide, polyurethane under the trademark PELLATHANE by Upjohn, polymethylpentene as sold under the trademark TPX by Mitsui and others.

The undersurface 26 of the body 25 is adapted to rest on the platform 20 of the signal generator 10 while the outer surface 27 is configured so as to extend the general outer configuration of the signal generator 10 when the surfaces 20 and 26 are mated. Extending from the platform 20 is a threaded stud 28 and hook member 29. An aperture 30 extends from the under surface 26 of body 25 and joins a second aperture 31 extending from the surface 27. The aperture 30 is large enough to accommodate the threaded stud 28 while the aperture 31 is large enough to accommodate a threaded nut 33. The junction of the aperture 30 and 31 forms a shoulder 32 on which the nut 33 rests. The nut 33 is provided with a slot 34 so that it may be tightened on the threaded stud 28 in known manner. Of course, other tools may be employed requiring a different configuration in the recess shown as slot 34. For example, a hexagonal recess may be employed in conjunction with a tool of hexagonal cross section.

A second aperture 36 extends into the body 25 from its face 37. The aperture 36 is adapted to accept the hook portion of hook 29 while the recess 38 on the face 37 is adapted to accept the lower portion of the hook 29. On assembly, the hook portion of hook 29 is inserted into the recess 36 to engage it side wall and the threaded stud 28 is inserted into the aperture 30. The nut 33 then engages the threads on the stud 28 and is tightened against the shoulder 32 to secure the body 25 to the platform 20 and signal generator 10. This assembly is illustrated in FIG. 2.

Contained within the body 25 are conductive terminals 40, one terminal for each lead 11. The illustrated embodiment is intended for bi-polar stimulation. However, for the purposes of clarity, only one lead 11 and one terminal 40 are shown. An aperture 41 extends from the face 37 of body 25 to the terminal 40 with an extension 41 extending from the terminal 40. The aperture 41 accepts the lead 11 and guides the pin 21 into electrical contact with the terminal 40. Similarly, an aperture 43 extends from the undersurface 26 of body 25 to the terminal 40 for the purpose of accepting and guiding the connection 19 into electrical contact with the terminal 40. The aperture 43 includes an enlarged portion 44 which accommodates the feed through 17. Similar apertures and terminals are provided for feed through 16 and connection 18. For example, an aperture 45 extends from face 37 to a terminal to accommodate a second lead. Aperture 53 in the surface 27 allow access to set screws 47 carried by the terminals 40 to lock pin 21 of lead 11 in position. Grommets 48 may be employed to seal the set screw apertures 53 while allowing access to the set screws, in known manner. Resilient washers 50 are provided which include a central aperture which accepts the connections 18 and 19 to rest atop the feed throughs 16 and 17. When the undersurface 26 of body 25 and platform 20 of generator 10 are mated, the shoulder formed between apertures 43 and 44 compresses the washers 50 against the top of feed throughs 16 and 17 to seal the connections 18 and 19 from the body environment.

Referring now to FIG. 3, there is illustrated a cross section of body 25 taken along the lines 3—3 in FIG. 2. As illustrated in FIG. 3, the terminal 40 includes a bore 51 which is adapted to accept pin 21 of lead 11. The aperture 41 of body 25 accepts the lead 11 and guides the pin 21 to and through the bore 51. If the body 25 is made of a transparent material, the extension of the pin 21 through the bore 40 and into the aperture 41' provides a visual assurance of proper placement of the pin 21 relative to the terminal 40. A second bore 52 in terminal 40 (see FIG. 4) receives the connection 19 of feed through 17, the aperture 43 accepting the connection 19 and guiding it to the bore 52. An extension 43' of aperture 43 may be provided to allow visual verification of proper positioning of the connection 19 relative to the terminal 40. In the illustration of FIG. 3, the lead 11 is not positioned within the aperture 41 or bore 51 so as to illustrate the intersection of the bores 51 and 52 within the terminal 40, the connection 19 being visible through the bore 51. As described above, an aperture 53 is provided for access to the set screw 47. Set screw may be provided on its end with a hexagonal recess for cooperation with a tool 54 (see FIG. 4) having a similar cross section at its terminus, in known manner.

FIG. 4 is a cross section taken along line 4—4 in FIG. 3 and further illustrates the intersection of the bores 51 and 52, the intersection preferably being in line with the set screw. That is, as the set screw 47 is tightened against the pin 21, pin 21 is urged against the connection 19 thereby securing both pin 21 and conection 19 in place within terminal 40. This further assures an electrical communication between the connection 19 and pin 21. However, other configurations may be employed so long as the pin 21 and connection 19 are in contact with each other or with the conductive terminal 40.

Obviously, many modifications and variations of the present invention are possible in light of the above teachings. For example, the hook 29 may be replaced by a threaded stud such as that illustrated at 28 to function in a manner similar to stud 28 to secure the body 25 to the platform 20 and signal generator 10. Other mechanical securement systems may also be employed consistent with the present invention. Additionally, an adhesive material may be employed between the undersurface 26 of body 25 and platform 20 of signal generator 10 to provide a redundant securement to the illustrated mechanical fasteners and a redundant seal to the seal provided by the resilient washers 50. Also, the aperture 43 need not guide the connection 19 through a bore in the terminal 40 but, instead, need only guide it into contact with that terminal 40. If the connection 19 is guided to a location adjacent to terminal 40, and the material for which the body 25 is made sufficiently transparent, the connection 19 and terminal 40 may be welded to each other through the body material by known techniques. Further, the connection 19 may be welded within the bore 52 of FIG. 4 through the aperture engaged by the set screw 47 with the set screw 47 removed. Modification to accommodate unipolar stimulation is within the skill of one ordinarily skilled in the art. Accordingly, within the scope of the appended claims, the invention may be practiced other than as specifically described.

What is claimed is:

1. In a body implantable stimulator of the type having signal generator means, including output means extending therefrom, having lead means, including contact means carried thereby, and having connector means electrically and mechanically interconnecting said lead means and signal generating means, the improvement wherein said connector means comprises preformed means including terminal means for interconnecting said output means and said contact means, said terminal means having first and second bore means and said preformed connector means comprising aperture means associated with each of said bore means, said aperture means accepting and guiding said contact means and output means into different ones of said first and second bore means, and further comprising mechanical fastener means for securing said preformed connector means to said signal generator means.

2. The stimulator of claim 1 wherein said mechanical fastener means comprise first means carried by said signal generator means and second means engaging said first means.

3. The signal generator assembly of claim 2 wherein said mechanical fastener means engage said preformed connector means at at least two spaced locations.

4. The signal generator assembly of claim 1 wherein said mechanical fastener means engage said preformed connector means at at least two spaced locations.

5. The stimulator of claim 4 wherein said mechanical fastener means comprise first means carried by said signal generator means and second means engaging said first means.

6. The stimulator of claim 1 wherein said contact means comprises pin means.

7. The stimulator of claim 6 wherein said first and second bore means intersect within said terminal means.

8. The stimulator of claim 7 wherein said terminal means further comprises means for locking said output means and pin means in said bore means.

9. The stimulator of claim 8 wherein said locking means engages said pin means to urge it against said output means.

10. The stimulator of claim 9 wherein said locking means comprises set screw means.

11. The stimulator of claim 1 wherein said terminal means further comprises means for locking said output means and contact means in said bore means.

12. The stimulator of claim 11 wherein said first and second bore means intersect within said terminal means.

13. The stimulator of claim 12 wherein said locking means further comprises weld means securing said output means within said first bore.

14. A body implantable stimulator of the type having a signal generator means, including output means carried thereby, and having connector means, including terminal means, carried by said signal generator means for electrically interconnecting said output means and said contact means, the improvement wherein said terminal means comprises bore means, said connector means comprising preformed means including first means for accepting and guiding said output means into said terminal means bore means.

15. The stimulator of claim 14 wherein said preformed connector means further comprises second means for accepting said lead means and guiding said contact means into contact with said terminal means.

16. The stimulator of claim 15 wherein said contact means comprises pin means.

17. The stimulator of claim 16 wherein said terminal means comprises second bore means, said second accepting and guiding means guiding said pin means into said second bore means.

18. The stimulator of claim 17 wherein said terminal means further comprises means for locking said output means and pin means in said bore means.

19. The stimulator of claim 17 wherein said first and second bore means intersect within said terminal means.

20. The stimulator of claim 19 wherein said terminal means further comprises means for locking said output means and pin means in said bore means.

21. The stimulator of claim 20 wherein said locking means engages said pin means to urge it against said output means.

22. The stimulator of claim 21 wherein said locking means comprises set screw means.

23. The stimulator of claim 22 wherein said locking means further comprises weld means securing said output means within said first bore.

24. The method of mechanically and electrically interconnecting a body implantable signal generator and a lead, the generator having output connections and the lead having a pin contact, comprising the steps of:
providing a terminal for each output connection and pin contact to be interconnected, said terminals having an output connection bore and a pin contact bore;
forming a connector body around said terminals including a passageway through said connector body to said output connection and pin contact terminal bores;
positioning said connector body on said signal generator while guiding said output connections through said passageways and into said pin contact terminal bores.

* * * * *

UNITED STATES PATENT AND TRADEMARK OFFICE
CERTIFICATE OF CORRECTION

PATENT NO. : 4,142,532
DATED : March 6, 1979
INVENTOR(S) : Lyle A. Ware

It is certified that error appears in the above-identified patent and that said Letters Patent are hereby corrected as shown below:

Claim 14, line 2, after "including output means" insert --extending therefrom, having lead means, including contact means--.

Claim 24, line 16, "bores." should be --bores;--.

Claim 24, after line 16 add the following lines:

--securing said connector body to said signal generator with mechanical fasteners; and inserting at least the pins of said leads through said passageways and into contact with said terminals.--

Signed and Sealed this

Third Day of July 1979

[SEAL]

Attest:

Attesting Officer

LUTRELLE F. PARKER
Acting Commissioner of Patents and Trademarks